United States Patent [19]
Eilam et al.

[11] Patent Number: 5,357,981
[45] Date of Patent: Oct. 25, 1994

[54] APPARATUS AND METHOD FOR THE PREVENTION OF SNORING

[76] Inventors: Zohar Eilam, 5 Blum Street, Ramat Aviv 69461; Yehuda Bergman, 8 Zaidman Street, Kiryat Ono 55238, both of Israel

[21] Appl. No.: 88,134

[22] Filed: Jul. 7, 1993

[51] Int. Cl.⁵ ............................................. A61F 5/56
[52] U.S. Cl. ..................................... 128/848; 128/897
[58] Field of Search ............................. 128/848, 897

[56] References Cited

U.S. PATENT DOCUMENTS

| | | | |
|---|---|---|---|
| 663,825 | 12/1900 | Wilson | 128/848 |
| 898,379 | 1/1908 | Liebhordt | 128/848 |
| 2,304,235 | 6/1941 | Boots | 128/848 |
| 4,586,506 | 5/1986 | Nangle | 128/DIG. 15 |

*Primary Examiner*—William E. Kamm
*Assistant Examiner*—Brian M. Green
*Attorney, Agent, or Firm*—Abelman, Frayne & Schwab

[57] ABSTRACT

A protrusion which is removably attachable to an exterior ventral surface of an article of clothing worn by a subject and which causes mild discomfort but no injury to a subject when the subject lies on his back, thereby urging the subject not to lie on his back when asleep.

12 Claims, 3 Drawing Sheets

FIG.1A
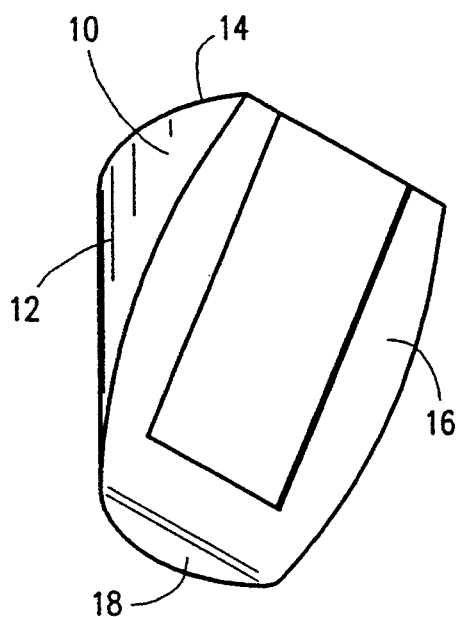
FIG.1B
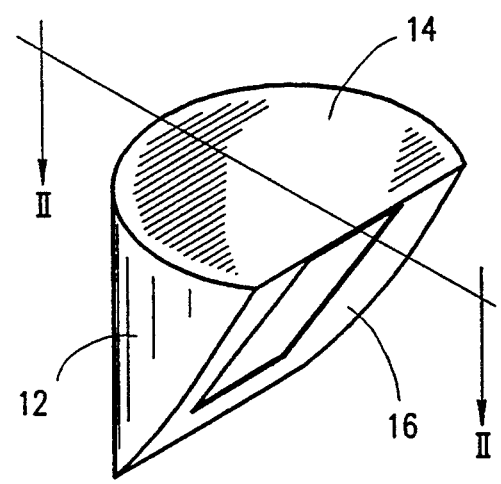
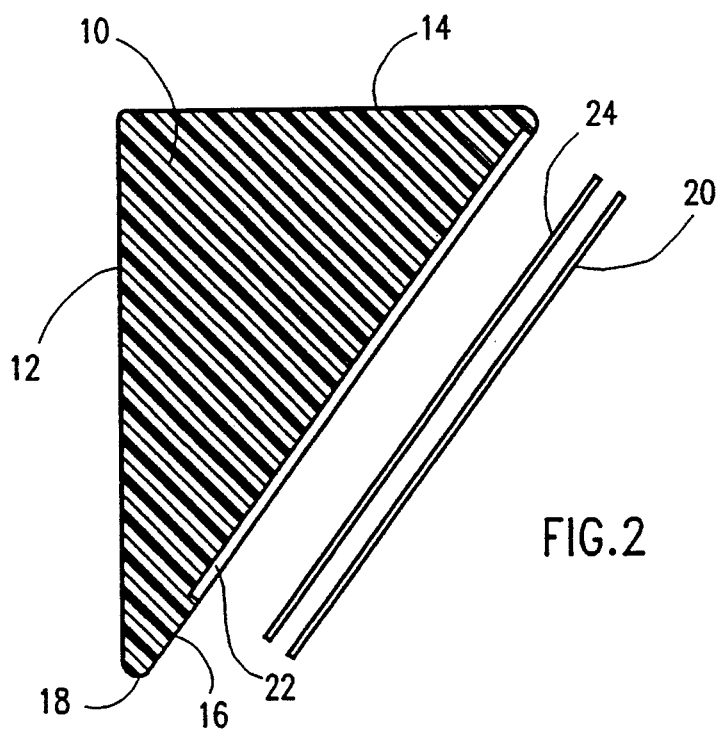
FIG.2

APPARATUS AND METHOD FOR THE PREVENTION OF SNORING

FIELD OF THE INVENTION

The present invention relates to the prevention of snoring.

BACKGROUND OF THE INVENTION

A great variety of techniques have been proposed for reducing or eliminating snoring. It is now commonly accepted that snoring which does not result from a medical abnormality can be significantly reduced if a subject is prevented from sleeping on his back.

SUMMARY OF THE INVENTION

The present invention seeks to provide apparatus and a method for preventing a person from sleeping on his or her back and thus reducing snoring.

There is thus provided in accordance with a preferred embodiment of the present invention a protrusion which is removably attachable to an exterior ventral surface of an article of clothing worn by a subject and which causes mild discomfort but no injury to a subject when the subject lies on his back, thereby urging the subject not to lie on his back when asleep.

In accordance with a preferred embodiment of the present invention, the protrusion comprises a transversely cut cylinder. Preferably, the transversely cut cylinder is a circular cylinder.

In accordance with a preferred embodiment of the present invention the transversely cut cylinder comprises a curved surface terminating at a perpendicular flat surface. An inclined, generally flat surface joins the curved surface and the perpendicular flat surface.

In accordance with a preferred embodiment of the invention, the tip of the generally flat surface is tapered.

Additionally in accordance with a preferred embodiment of the present invention an area of fastening material is fixedly attached to the inclined generally flat surface. Preferably, the fastening hook material is located in a recess formed in the inclined generally flat surface. It may be attached therein by means of adhesive material. The fastening material is preferably Velcro (R).

Further in accordance with a preferred embodiment of the present invention, the protrusion is formed of a foamed plastic material having a Shore-A hardness of between 40 and 65 and preferably 60. The plastic material is preferably foamed polyurethane or foamed polyethylene.

Additionally in accordance with a preferred embodiment of the present invention, there is provided an area of fastening material on the clothing at a desired location for removable fastening cooperation with the area of fastening material on the protrusion.

BRIEF DESCRIPTION OF THE DRAWINGS

The present invention will be understood and appreciated more fully from the following detailed description, taken in conjunction with the drawing in which:

FIGS. 1A and 1B are pictorial illustrations of a protrusion constructed and operative in accordance with a preferred embodiment of the present invention;

FIG. 2 is an exploded view sectional illustration taken along the lines II—II of FIG. 1B;

DETAILED DESCRIPTION OF A PREFERRED EMBODIMENT

Figure 3B:
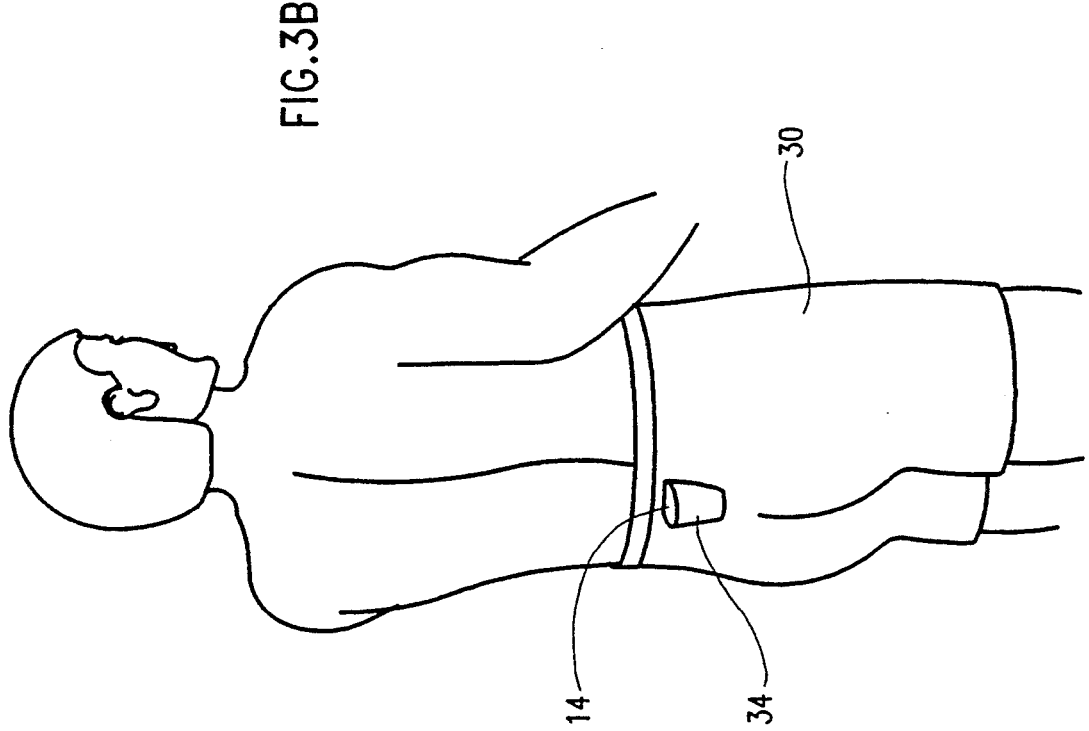
FIGS. 3A and 3B illustrate apparatus for preventing snoring in detached and attached arrangement.

Reference is now made to FIGS. 1A and 1B, which are pictorial illustrations of a protrusion constructed and operative in accordance with a preferred embodiment of the present invention and to FIG. 2, which is an exploded view sectional illustration taken along the lines II—II of FIG. 1B.

As seen in FIGS. 1A, 1B and 2, the anti-snoring protrusion preferably comprises a transversely cut circular cylinder 10 having a curved cylindrical surface 12 terminating at a perpendicular flat surface 14. An inclined, generally flat surface 16 joins the curved surface 12 and the perpendicular flat surface 14.

In accordance with a preferred embodiment of the invention, the tip 18 of the generally flat surface 16 is tapered.

Additionally in accordance with a preferred embodiment of the present invention a planar portion 20 of fastening material, such as preferably the hook material of velcro R, is fixedly attached to the inclined generally flat surface 16. Preferably, the fastening hook material is located in a recess 22 formed in the inclined generally flat surface 16. It may be attached therein by means of a sheet of adhesive material 24.

Further in accordance with a preferred embodiment of the present invention, the protrusion is formed as a solid element of a foamed plastic material having a Shore hardness of between 50 and 70 and preferably 60. The plastic material is preferably foamed polyurethane or foamed polyethylene.

Preferably the diameter of the cylinder 10 is approximately 55 mm, the length of surface 16 is approximately mm and the weight of the protrusion is approximately 30 grams.

Figure 3A:
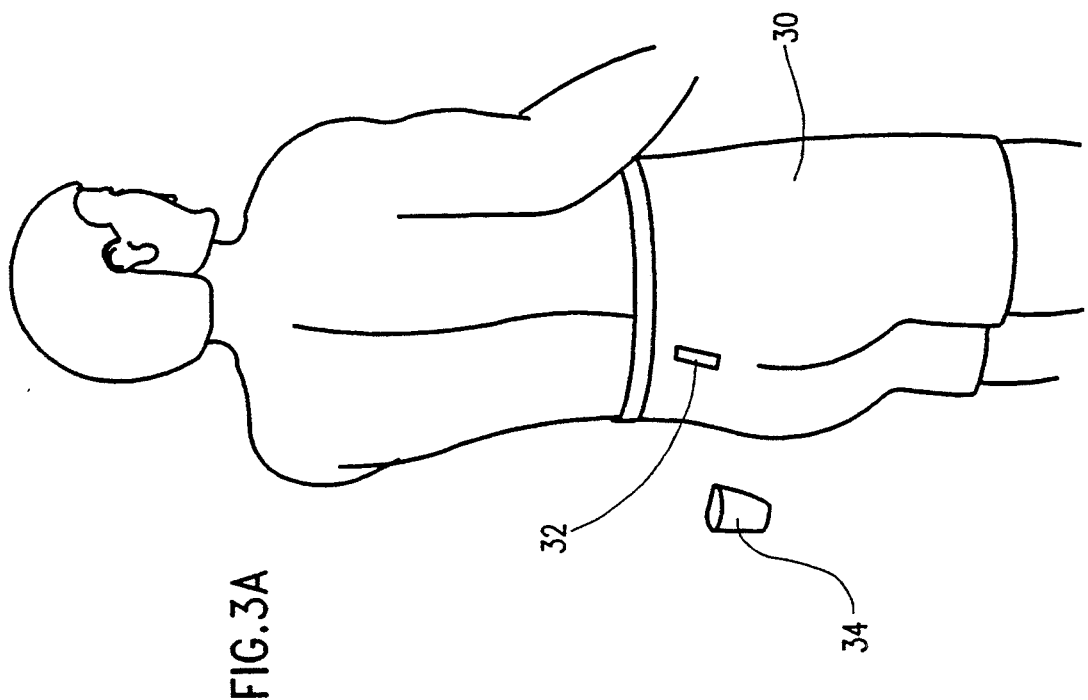

Reference is now made to FIGS. 3A and 3B which illustrate apparatus for preventing snoring. The apparatus comprises a garment 30, which may be an undergarment or sleepwear for men or women. Preferably there is provided an area 32 of fastening material, such as felt or other material which is removably and reliably attached to by Velcro R hook material or the like, fixedly attached to the garment at a desired location on the ventral portion of the garment, preferably just above the coccyx.

FIG. 3A shows a protrusion 34, preferably of the type shown in FIG. 3A, separate from the area 32 of the fastening material, and FIG. 3B shows the protrusion attached, with the flat surface 14 facing upward.

Figure 4A:
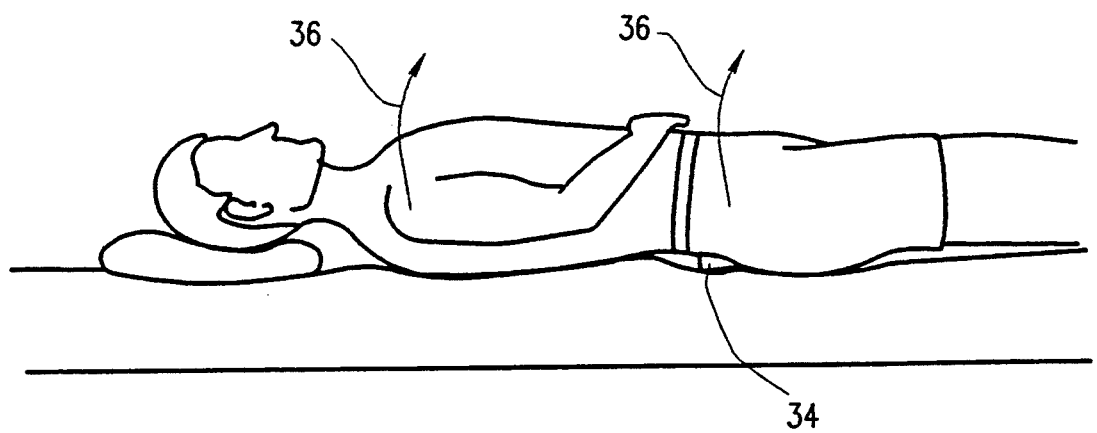
FIGS. 4A and 4B illustrate the operation of the apparatus of FIGS. 1A–3B in preventing snoring.
Figure 4B:
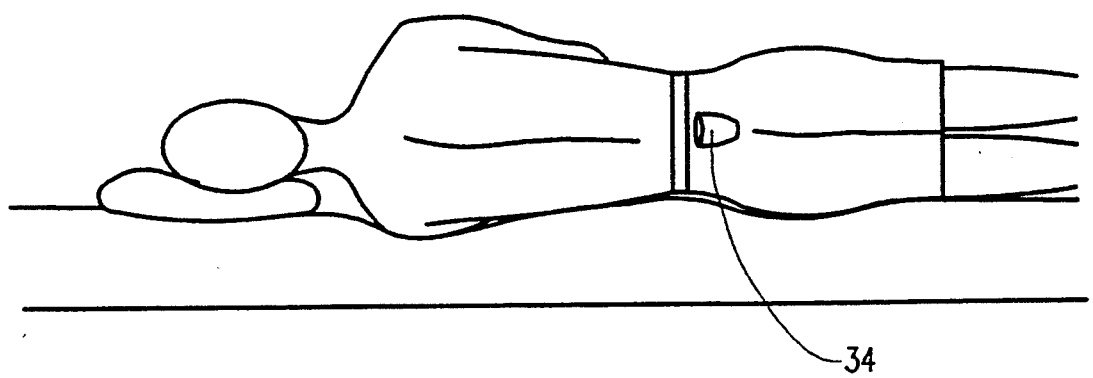

Reference is now made to FIGS. 4A and 4B which illustrate the operation of the apparatus of FIGS. 1A–3B in preventing snoring. It is seen that when a subject lies on his back, the protrusion 34 is disposed in the small of his back and causes discomfort but no injury or damage to the bed, due to its curved configuration. This discomfort tends to cause the subject to roll over, as indicated by the arrows 36 in FIG. 4A, to a side position as shown in FIG. 4B or to any other position other than that shown in FIG. 4A.

In this way, snoring which is intensified when the subject sleeps on his back is reduced or eliminated.

It will be appreciated by persons skilled in the art that the present invention is not limited by what has been particularly shown and described hereinabove. Rather the scope of the invention is defined only by the claims which follow:

We claim:

1. A protrusion which is removably attachable to an exterior ventral surface of an article of clothing worn by a subject and is arranged to protrude outwardly from said ventral surface and to cause mild discomfort but no injury to a subject when the subject lies on his back, thereby urging the subject not to lie on his back when asleep, said protrusion comprising a transversely cut generally circular cylinder defined about a cylinder axis, which defines a generally flat ventral surface engagement portion which is inclined with respect to said cylinder axis and a curved cylindrical surface which terminates in a flat surface, perpendicular to said cylinder axis.

2. A protrusion according to claim 1 and wherein said inclined, generally flat surface joins the curved surface and the perpendicular flat surface.

3. A protrusion according to claim 2 and wherein said inclined generally flat surface is formed with a tapered tip.

4. A protrusion according to claim 1 and also comprising fastening material fixedly attached to the inclined, generally flat surface of said protrusion.

5. A protrusion according to claim 4 wherein said inclined, generally flat fastening material is located in a recess formed in said surface.

6. A protrusion according to claim 1 wherein said protrusion is formed of a foamed plastic material having a Shore hardness of between 50 and 70.

7. A protrusion according to claim 6 and wherein said protrusion has a Shore hardness of approximately 60.

8. A protrusion according to claim 6 wherein said plastic material is selected from foamed polyurethane and foamed polyethylene.

9. A protrusion according to claim 4 also comprising an article of clothing having an area of fastening material thereon at a desired location for removable fastening cooperation with the area of fastening material on the protrusion.

10. A protrusion according to claim 1 wherein said cylinder has a diameter of approximately 55 mm.

11. A protrusion according to claim 1 wherein said protrusion has a weight of approximately 30 gram.

12. A method for preventing snoring comprising the steps of providing a protrusion comprising a transversely cut generally circular cylinder defined about a cylinder axis, which defines a generally flat ventral surface engagement portion which is inclined with respect to said cylinder axis and a curved cylindrical surface which terminates in a flat surface, perpendicular to said cylinder axis;

removably attaching the protrusion to an exterior ventral surface of an article of clothing worn by a subject, whereby said inclined, generally flat surface is attached to the ventral surface of the article of clothing and the curved surface extends outwardly therefrom, whereby mild discomfort but no injury is caused to a subject when the subject lies on his back, thereby urging the subject not to lie on his back when asleep.

* * * * *